United States Patent [19] [11] Patent Number: 5,939,515
Guenther et al. [45] Date of Patent: Aug. 17, 1999

[54] MODIFIED MELAMINE-FORMALDEHYDE RESINS

[75] Inventors: Erhard Guenther, Hassloch; Wolfgang Reuther, Heidelberg, both of Germany

[73] Assignee: BASF Aktiengesellschaft, Ludwigshafen, Germany

[21] Appl. No.: 09/000,390

[22] PCT Filed: Jul. 30, 1996

[86] PCT No.: PCT/EP96/03352

§ 371 Date: Jan. 29, 1998

§ 102(e) Date: Jan. 29, 1998

[87] PCT Pub. No.: WO97/07149

PCT Pub. Date: Feb. 27, 1997

[30] Foreign Application Priority Data

Aug. 17, 1995 [DE] Germany .......................... 195 30 178

[51] Int. Cl.$^6$ .................................................. C08G 12/30
[52] U.S. Cl. .......................... 528/254; 528/129; 528/163; 528/230; 264/45.8; 264/46.8
[58] Field of Search .................................... 528/163, 129, 528/254; 264/501, 45.8, 46.8

[56] References Cited

U.S. PATENT DOCUMENTS 4,088,620 5/1978 Nihongi et al. .
5,322,915 6/1994 Weiser et al. .......................... 528/163

FOREIGN PATENT DOCUMENTS 355 760 2/1990 European Pat. Off. .
523 485 1/1993 European Pat. Off. .
29 15 457 10/1980 Germany .
61 236834 10/1986 Japan .

OTHER PUBLICATIONS

Houben–Weyl, Bd. 14/2, S. 357 (no date).

*Primary Examiner*—Duc Truong
*Attorney, Agent, or Firm*—Keil & Weinkauf

[57] ABSTRACT

Condensation of products obtained by condensation of a mixture comprising
(A) from 90 to 99.9 mol % of a mixture consisting essentially of
  (a) from 30 to 100 mol % of melamine and
  (b) from 0 to 70 mol % of a substituted melamine of the formula I

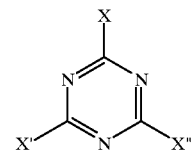

where X, X' and X" are as defined in the specification, or mixtures of melamines I, and
  (c) from 1 to 70 mol %, based on (a)+(b), of a substituted triazine of the formula II

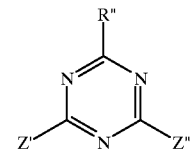

where R", Z' and Z" are as defined in the specification, or mixtures of triazines II, and
(B) from 0.1 to 10 mol %, based on (A) (a), (A) (b) and (B), of phenols which are unsubstituted or are substituted by radicals selected from the group consisting of $C_1$–$C_9$-alkyl and hydroxyl, $C_1$–$C_4$-alkanes substituted by two or three phenol groups, di(hydroxyphenyl)sulfones or mixtures of these phenols,
with
formaldehyde or formaldehyde-supplying compounds in a molar ratio of melamine, substituted melamine I and triazine II to formaldehyde within the range from 1:1.15 to 1:4.5, are useful for making molded articles.

8 Claims, No Drawings

MODIFIED MELAMINE-FORMALDEHYDE RESINS

The invention relates to condensation products obtainable by condensation of a mixture comprising as essential components (A) from 90 to 99.9 mol % of a mixture consisting essentially of (a) from 30 to 100 mol % of melamine and
(b) from 0 to 70 mol % of a substituted melamine of the general formula I

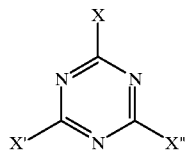

where X, X' and X" are each selected from the group consisting of —NH$_2$, —NHR and —NRR', and X, X' and X" are not all —NH$_2$, and R and R' are each selected from the group consisting of hydroxy-C$_2$–C$_{10}$-alkyl, hydroxy-C$_2$–C$_4$-alkyl(oxa-C$_2$–C$_4$-alkyl)$_n$, where n is from 1 to 5, and amino-C$_2$–C$_{12}$-alkyl, or mixtures of melamines I, and c) from 1 to 70 mol %, based on (a)+(b), of a substituted triazine of the general formula II

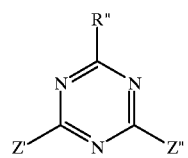

where R" is methyl or phenyl, Z' and Z" are each selected from the group consisting of —NH$_2$, —NHR$^{III}$ and NR$^{III}$R$^{IV}$, and R$^{III}$ and R$^{IV}$ are each selected from the group consisting of hydroxy-C$_2$–C$_{10}$-alkyl, hydroxy-C$_2$–C$_4$-alkyl-(oxa-C$_2$–C$_4$-alkyl)$_n$, where n is from 1 to 5, —CH$_2$CH$_2$—S—CH$_2$CH$_2$OH, and amino-C$_2$–C$_{12}$-alkyl, or mixtures of triazines II, and B) from 0.1 to 10 mol %, based on (A) (a), (A) (b) and (B), of phenols which are unsubstituted or are substituted by radicals selected from the group consisting of C$_1$–C$_9$-alkyl and hydroxyl, C$_1$–C$_4$-alkanes substituted by two or three phenol groups, di(hydroxyphenyl) sulfones or mixtures of these phenols, with formaldehyde or formaldehyde-supplying compounds in a molar ratio of melamine, substituted melamine I or triazine II to formaldehyde within the range from 1:1.15 to 1:4.5.

The invention further relates to a process for producing these condensation products, their use for producing fibers and foams, and molded articles obtainable from these products.

EP-A-523 485 describes condensation products obtainable by condensation of a mixture comprising as essential components (A) from 90 to 99.9 mol % of a mixture consisting essentially of (a) from 30 to 99 mol % of melamine and
(b) from 1 to 70 mol % of a substituted melamine of the general formula I

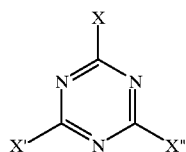

where X, X' and X" are each selected from the group consisting of —NH$_2$, —NHR and —NRR', and X, X' and X" are not all —NH$_2$, and R and R' are each selected from the group consisting of hydroxy-C$_2$–C$_4$-alkyl-, hydroxy-C$_2$–C$_4$-alkyl(oxa-C$_2$–C$_4$-alkyl)$_n$, where n is from 1 to 5, and amino-C$_2$–C$_{12}$-alkyl, or mixtures of melamines I, and B) from 0.1 to 10 mol %, based on (A) and (B), of phenols which are unsubstituted or are substituted by radicals selected from the group consisting of C$_1$–C$_9$-alkyl and hydroxyl, C$_1$–C$_4$-alkanes substituted by two or three phenol groups, di(hydroxyphenyl) sulfones or mixtures of these phenols, with formaldehyde or formaldehyde-supplying compounds in a molar ratio of melamines to formaldehyde within the range from 1:1.15 to 1:4.5, their use for producing fibers and foams, and molded articles obtainable from these products. The disadvantage of the fibers of EP-A-523 485 is that they lack extensibility.

It is an object of the present invention to provide melamineformaldehyde condensation products possessing improved fiber extensibility in the cured state.

We have found that this object is achieved by the above-defined condensation products.

We have also found a process for producing these condensation products, their use for producing fibers and foams, and also molded articles obtainable from these products.

The melamine resins of the invention include as monomeric building block (A) from 90 to 99.9 mol % of a mixture consisting essentially of from 30 to 100, preferably 50 to 99, particularly preferably from 85 to 95, mol % of melamine and from 0 to 70, preferably from 1 to 50, particularly preferably from 5 to 15, mol % of a substituted melamine I or mixtures of substituted melamines I and also from 1 to 70, preferably from 1 to 40, particularly preferably from 1 to 25, mol %, based on (a)+(b), of a substituted triazine II.

As further monomeric building block (B) the melamine resins include from 0.1 to 10 mol %, based on the total number of moles of monomeric building blocks (A) (a), (A) (b) and (B), of a phenol or of a mixture of phenols.

The condensation products of the invention are obtainable by reacting the components (A) and (B) with formaldehyde or formaldehyde-supplying compounds in a molar ratio of melamine, substituted melamine I and triazine II to formaldehyde within the range from 1:1.15 to 1:4.5, preferably from 1:1.8 to 1:3.0.

Suitable substituted melamines of the general formula I

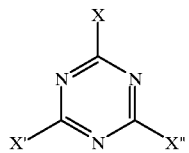

are those in which X, X' and X" are each selected from the group consisting of —$NH_2$, —NHR and —NRR', and X, X' and X" are not all —$NH_2$, and R and R' are each selected from the group consisting of hydroxy-$C_2$–$C_{10}$-alkyl, hydroxy-$C_2$–$C_4$-alkyl(oxa-$C_2$–$C_4$-alkyl)$_n$, where n is from 1 to 5, and amino-$C_2$–$C_{12}$-alkyl.

Preferred hydroxy-$C_2$–$C_{10}$-alkyl includes hydroxy-$C_2$–$C_6$-alkyl such as 2-hydroxyethyl, 3-hydroxy-n-propyl, 2-hydroxyisopropyl, 4-hydroxy-n-butyl, 5-hydroxy-n-pentyl, 6-hydroxy-n-hexyl, 3-hydroxy-2,2-dimethylpropyl, preferably hydroxy-$C_2$–$C_4$-alkyl such as 2-hydroxyethyl, 3-hydroxy-n-propyl, 2-hydroxyisopropyl and 4-hydroxy-n-butyl, particularly preferably 2-hydroxyethyl and 2-hydroxyisopropyl.

Preferred hydroxy-$C_2$–$C_4$-alkyl(oxa-$C_2$–$C_4$-alkyl)$_n$, groups are those with n from 1 to 4, particularly preferably those with n=1 or 2 such as 5-hydroxy-3-oxapentyl, 5-hydroxy-3-oxa-2,5-dimethylpentyl, 5-hydroxy-3-oxa-1,4-dimethylpentyl, 5-hydroxy-3-oxa-1,2,4,5-tetramethylpentyl, 8-hydroxy-3,6-dioxaoctyl.

Amino-$C_2$–$C_{12}$-alkyl is preferably amino-$C_2$–$C_8$-alkyl such as 2-aminoethyl, 3-aminopropyl, 4-aminobutyl, 5-aminopentyl, 6-aminohexyl, 7-aminoheptyl and 8-aminooctyl, particularly preferably 2-aminoethyl and 6-aminohexyl, very particularly preferably 6-aminohexyl.

The following compounds are substituted melamines I which are particularly useful for this invention:

2-hydroxyethylamino-substituted melamines such as 2-(2-hydroxyethylamino)-4,6-diamino-1,3,5-triazine, 2,4-di-(2-hydroxyethylamino)-6-amino-1,3,5-triazine, 2,4,6-tris-(2-hydroxyethylamino)-1,3,5-triazine, 2-hydroxyisopropylamino-substituted melamines such as 2-(2-hydroxyisopropylamino)-4,6-diamino-1,3,5-triazine, 2,4-di-(2-hydroxyisopropylamino)-6-amino-1,3,5-triazine, 2,4,6-tris-(2-hydroxyisopropylamino)-1,3,5-triazine, 5-hydroxy-3-oxapentylamino-substituted melamines such as 2-(5-hydroxy-3-oxapentylamino)-4,6-diamino-1,3,5-triazine, 2,4-di-(5-hydroxy-3-oxapentylamino)-6-amino-1,3,5-triazine, 2,4,6-tris-(5-hydroxy-3-oxapentylamino)-1,3,5-triazine, 6-aminohexylamino-substituted melamines such as 2-(6-aminohexylamino)-4,6-diamino-1,3,5-triazine, 2,4-di-(6-aminohexylamino)-6-amino-1,3,5-triazine, 2,4,6-tris-(6-aminohexylamino)-1,3,5-triazine or mixtures of these compounds, for example a mixture of 10 mol % of 2-(5-hydroxy-3-oxapentylamino)-4,6-diamino-1,3,5-triazine, 50 mol % of 2,4-di-(5-hydroxy-3-oxapentylamino)-6-amino-1,3,5-triazine and 40 mol % of 2,4,6-tris-(5-hydroxy-3-oxapentyl-amino)-1,3,5-triazine.

Suitable substituted triazines of the general formula II

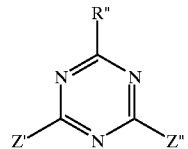

are those where R" is methyl or phenyl, Z' and Z" are each selected from the group consisting of —$NH_2$, —NHR$^{III}$ and —NR$^{III}$R$^{IV}$, and R$^{III}$ and R$^{IV}$ are each selected from the group consisting of hydroxy-$C_2$–$C_{10}$-alkyl, hydroxy-$C_2$–$C_4$-alkyl(oxa-$C_2$–$C_4$-alkyl)$_n$, where n is from 1 to 5, —$CH_2CH_2$—S—$CH_2CH_2OH$, and amino-$C_2$–$C_{12}$-alkyl.

Preferred hydroxy-$C_2$–$C_{10}$-alkyl includes hydroxy-$C_2$–$C_6$-alkyl such as 2-hydroxyethyl, 3-hydroxy-n-propyl, 2-hydroxyisopropyl, 4-hydroxy-n-butyl, 5-hydroxy-n-pentyl, 6-hydroxy-n-hexyl, 3-hydroxy-2, 2-dimethylpropyl, preferably hydroxy-$C_2$–$C_4$-alkyl such as 2-hydroxyethyl, 3-hydroxy-n-propyl, 2-hydroxyisopropyl and 4-hydroxy-n-butyl, particularly preferably 2-hydroxyethyl and 2-hydroxyisopropyl.

Preferred hydroxy-$C_2$–$C_4$-alkyl(oxa-$C_2$–$C_4$-alkyl)$_n$ groups are those with n from 1 to 4, preferably those with n=1 or 2, such as 5-hydroxy-3-oxapentyl, 5-hydroxy-3-oxa-2,5-dimethylpentyl, 5-hydroxy-3-oxa-1,4-dimethylpentyl, 5-hydroxy-3-oxa-1,2,4,5-tetramethylpentyl, 8-hydroxy-3,6-dioxaoctyl.

Amino-$C_2$–$C_{12}$-alkyl is preferably amino-$C_2$–$C_8$-alkyl such as 2-aminoethyl, 3-aminopropyl, 4-aminobutyl, 5-aminopentyl, 6-aminohexyl, 7-aminoheptyl and 8-aminooctyl, particularly preferably 2-aminoethyl and 6-aminohexyl, very particularly preferably 6-aminohexyl.

The following compounds are substituted triazines II particularly suitable for this invention:

2,4-(di-5-hydroxy-3-oxapentylamino)-6-methyl-1,3,5-triazine,
2,4-(di-5-hydroxy-3-thiopentylamino)-6-methyl-1,3,5-triazine,
2,4-(di-5-hydroxy-3-oxapentylamino)-6-phenyl-1,3,5-triazine,
2,4-(di-5-hydroxy-3-thiopentylamino)-6-phenyl-1,3,5-triazine,
2,4-(di-5-hydroxy-3-oxaethylamino)-6-methyl-1,3,5-triazine,
2,4-(di-5-hydroxy-3-thioethylamino)-6-methyl-1,3,5-triazine,
2,4-(di-5-hydroxy-3-oxaethylamino)-6-phenyl-1,3,5-triazine,
2,4-(di-5-hydroxy-3-thioethylamino)-6-phenyl-1,3,5-triazine.

The substituted triazines II are obtainable by amine exchange of the corresponding 6-substituted 2,4-diamino-1,3,5-triazines with the corresponding primary amines R$^{III}$NH$_2$ and R$^{IV}$NH$_2$. Customarily, the amine exchange is carried out at temperatures within the range from 100 to 220° C., preferably from 120 to 200° C., advantageously under atmospheric pressure.

The reaction can be carried out in the presence of solvents, preferably polyols, such as ethylene glycol, 1,2-propylene glycol, diethylene glycol or triethylene glycol.

The molar ratio of amine, R$^{III}$NH$_2$ or R$^{IV}$NH$_2$ to triazine is customarily chosen within the range from 3.0:1 to 8.0:1, preferably from 4.0:1 to 5.0:1. Particular preference is given to the procedure where the amine is used in excess, so that the further addition of a solvent can be dispensed with.

In a preferred embodiment, the amino exchange is carried out in the presence of acid catalysts, in particular with strong and medium protic acids such as hydrofluoric acid, hydrochloric acid, hydrobromic acid, sulfuric acid, nitric acid, phosphoric acid, sulfamic acid, thiocyanic acid, p-toluenesulfonic acid or methanesulfonic acid and also Lewis acids such as boron trifluoride, aluminum chloride, tin(IV) chloride, antimony(V) fluoride or iron(III) bromide.

However, from observations to date, the presence of a catalyst is not absolutely necessary with guanamines.

The course of the reaction is advantageously monitored using analytical methods, a preferred possibility being HPLC.

If the amino exchange is carried out in the presence of one of the aforementioned catalysts, the triazines II are generally isolated by neutralizing with a customary base such as an alkali metal hydroxide, especially sodium hydroxide or potassium hydroxide, and then separating off the precipitated salts.

Excess amine can be distilled off at reduced pressure (from 0.1 to 100 mbar, preferably from 10 to 20 mbar) at a temperature within the range from 100 to 300° C., preferably from 100 to 200° C., depending on the boiling point of the amine used.

Suitable phenols (B) include phenols containing one or two hydroxyl groups, such as unsubstituted phenols, phenols substituted by radicals selected from the group consisting of $C_1$–$C_9$-alkyl and hydroxyl, and also $C_1$–$C_4$-alkanes substituted by two or three phenol groups, di(hydroxyphenyl) sulfones, and mixtures thereof.

Preferred phenols include phenol, 4-methylphenol, 4-tert-butylphenol, 4-n-octylphenol, 4-n-nonylphenol, pyrocatechol, resorcinol, hydroquinone, 2,2-bis(4-hydroxyphenyl)propane, 4,4'-dihydroxydiphenylsulfone, particularly preferably phenol, resorcinol and 2,2-bis(4-hydroxyphenyl)propane.

Formaldehyde is generally used as an aqueous solution having a concentration of, for example, from 40 to 50% by weight or in the form of compounds that supply formaldehyde in the course of the reaction with (A) and (B), for example as oligomeric or polymeric formaldehyde in solid form, such as paraformaldehyde, 1,3,5-trioxane or 1,3,5,7-tetroxocane.

Fibers are produced using advantageously from 1 to 50, preferably from 5 to 15, in particular from 7 to 12, mol % of the substituted melamine I, from 1 to 25 mol % of substituted triazine II, and also from 0.1 to 9.5, preferably from 1 to 5, mol % of one of the above-recited phenols or mixtures thereof.

Foams are produced using advantageously from 0.5 to 20, preferably from 1 to 10, in particular from 1.5 to 5, mol % of the substituted melamine I, from 1 to 25 mol % of substituted triazine II or mixtures thereof, and also from 0.1 to 5, preferably from 1 to 3, mol % of one of the above-recited phenols or mixtures thereof.

The resins are produced by polycondensing melamine, substituted melamine I, substituted triazine II and phenol together with formaldehyde or formaldehyde-supplying compounds, either having all components present from the start or adding them portionwise and gradually to the reaction and subsequently adding further melamine, substituted melamine or phenol to the precondensates formed.

The polycondensation is typically carried out in a conventional manner (see EP-A 355 760, Houben-Weyl, vol. 14/2, p. 357 et seq.).

The reaction temperatures used are generally chosen within the range from 20 to 150° C., preferably from 40 to 140° C.

The reaction pressure is typically uncritical. In general, the pressure employed is within the range from 100 to 500 kPa, preferably from 100 to 300 kPa.

The reaction can be carried out with or without solvent. Typically, no solvent is added when aqueous formaldehyde solution is used. If formaldehyde bound in solid form is used, water is usually used as solvent, and the amount used is typically within the range from 5 to 40, preferably from 15 to 25, % by weight based on the total amount of monomer used.

Furthermore, the polycondensation is generally carried out within a pH range above 6. Preference is given to the pH range from 7.5 to 10.0, particularly preferably from 8 to 10.

Moreover, the reaction mixture may include small amounts of customary additives such as alkali metal sulfites, for example sodium disulfite and sodium sulfite, alkali metal formates, for example sodium formate, alkali metal citrates, for example sodium citrate, phosphates, polyphosphates, urea, dicyandiamide or cyanamide. They can be added as pure individual compounds or as mixtures with one another, in each case without a solvent or as aqueous solutions, before, during or after the condensation reaction.

Other modifiers are amines and also amino alcohols such as diethylamine, ethanolamine, diethanolamine or 2-diethylaminoethanol.

Suitable further additives include fillers, emulsifiers or blowing agents.

As fillers it is possible to use for example fibrous or pulverulent inorganic reinforcing agents or fillers such as glass fibers, metal powders, metal salts or silicates, for example kaolin, talc, baryte, quartz or chalk, also pigments and dyes. Emulsifiers used are generally the customary nonionic, anionic or cationic organic compounds having long-chain alkyl radicals. If the uncured resins are to be processed into foams, it is possible to use pentane, for example, as blowing agent.

The polycondensation is generally carried out batchwise or continuously, for example in an extruder (see EP-A 355 760), in a conventional manner.

The production of molded articles by curing the condensation products of this invention is effected in a conventional manner by adding small amounts of acids such as formic acid, sulfuric acid or ammonium chloride.

Foams can be produced by foaming an aqueous solution or dispersion which contains the uncured condensate, an emulsifier, a blowing agent and a curing agent, optionally with customary additives, as listed above, and then curing the foam. Such a process is described in detail in DE-A 29 15 457.

Fibers are generally produced by spinning the melamine resin of the invention in a conventional manner, for example following addition of a curing agent, at room temperature, in a roto-spinning apparatus and subsequently curing the crude fibers in a heated atmosphere, or by spinning in a heated atmosphere, simultaneously evaporating the water used as solvent and curing the condensate. Such a process is described in detail in DE-A 23 64 091.

The advantage of the process of this invention is the making available of melamine-formaldehyde fibers having improved extensibility properties.

EXAMPLES

To determine the weight loss by hydrolysis, the resins were exposed to boiling water (100° C.) for 24 h. The resin was weighed before and after hydrolysis and the (relative) weight loss was calculated from the difference between the measured values and the starting weight.

The tenacity and elongation were determined by the method of PM-T 4001-82.

Example 1

(Preparation of Triazine II)

500.56 g of acetoguanamine, 1682.4 g of aminoethoxyethanol and 106.8 g of ammonium chloride were stirred at 175° C. for 60 h. The progress of the reaction was monitored by HPLC (C18 column 5 μm, eluent: 1 g of $KHPO_4$/237 g of MeOH/700 g of $H_2O$). The reaction mixture was then cooled down to 80° C. and the ammonium chloride used was neutralized with sodium hydroxide solution (50% strength). Sodium chloride formed was filtered off with suction, and the excess amine remaining in solution was distilled off (170° C./15 mbar). This produced 1170 g of a colorless resin (91.4%) consisting of 2, 4-di(5-hydroxy-3-oxapentylamino)-6-methyl-1,3,5-triazine.

Example 2

(Resin with both Triazine I and Triazine II)

1663 g of melamine, 678.65 g of an 80% strength mixture of 10 mol % of 2-(5-hydroxy-3-oxypentylamino)-4,6-diamino-1,3,5-triazine, 50 mol % of 2,4-di(5-hydroxy-3-oxapentylamino)-6-amino-1,3,5-triazine and 40 mol % of 2,4,6-tri(5-hydroxy-3-oxapentylamino)-1,3,5-triazine in water ("HOM"), 206.42 g of acetoguanamine, 1207 g of formaldehyde (40% strength), 507.2 g of paraformaldehyde, 37.62 g of bisphenol A and 8.25 g of diethylethanolamine were stirred at 98° C. for 140 min to a viscosity of 470 Pas. The mixture was then cooled down with ice to RT. After addition of 1% strength formic acid, the resin was spun into fibers in a conventional manner (see EP-A 523 485).

AATCC: 205 ppm (formaldehyde content)
Weight loss by hydrolysis (24 h at 100° C.): 2.8%
Tenacity: 388 N/mm$^2$
Elongation: 32.7%

Example 3

(Resin with just Triazine II)

1871.1 g of melamine, 496.7 g of triazine II from Example 1, 1414.7 g of 40% strength aqueous formaldehyde, 424.1 g of paraformaldehyde, 37.6 g of bisphenol A and 8.25 ml of diethylethanolamine were stirred at 980C for 142 min to a viscosity of 450 Pas. The mixture was then rapidly cooled down to RT. Following addition of 1% strength formic acid, the resin was spun into fibers in a conventional manner (see Example 2).

AATAATCC: 125 ppm
Weight loss by hydrolysis (24 h at 100° C.): 2.3%
Tenacity: 558 N/mm$^2$
Elongation: 30%

Comparative Example (Resin without Triazine II)

A mixture of 1871 g of melamine, 620 g of an 80% strength by weight HOM mixture (see Example 2), 472.8 g of paraformaldehyde, 38.2 g of phenol and 15.4 ml of diethylethanolamine were condensed at 98° C. for 150 min to a viscosity of 500 Pas. Following addition of 1% strength by weight formic acid, the resin was spun into fibers in a conventional manner (see Example 2).

AATCC: 253 ppm
Weight loss by hydrolysis: 2.5%
Tenacity: 427 N/mm$^2$
Elongation: 21[{]ps

We claim:

1. A process for producing a condensation product, which process comprises condensing
(A) from 90 to 99.9 mol % of a mixture consisting essentially of
   (a) from 30 to 100 mol % of melamine and
   (b) from 0 to 70 mol % of a substituted melamine of the formula I

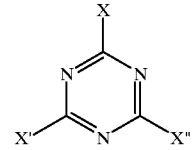

where X, X' and X" are each selected from the group consisting of —$NH_2$, —NHR and —NRR'; and X, X' and X" are not all —$NH_2$; and R and R' are each selected from the group consisting of hydroxy-$C_2$–$C_{10}$-alkyl, hydroxy-$C_2$–$C_4$-alkyl(oxa-$C_2$–$C_4$-alkyl)$_n$, where n is from 1 to 5, and amino-$C_2$–$C_{12}$-alkyl, or mixtures of melamines I, and
   c) from 1 to 70 mol %, based on (a)+(b), of a substituted triazine of the formula II

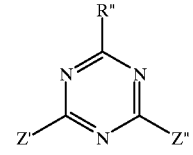

where R" is methyl or phenyl, Z' and Z" are each selected from the group consisting of —$NH_2$, —NHR$^{III}$ and NR$^{III}$R$^{IV}$, and R$^{III}$ and R$^{IV}$ are each selected from the group consisting of hydroxy-$C_2$–$C_{10}$-alkyl, hydroxy-$C_2$–$C_4$-alkyl (oxa-$C_2$–$C_4$-alkyl)$_n$, where n is from 1 to 5, —$CH_2CH_2$—S—$CH_2CH_2OH$, and amino-$C_2$–$C_{12}$-alkyl, or mixtures of triazines II, and
B) from 0.1 to 10 mol %, based on (A) (a), (A) (b) and (B), of phenols which are unsubstituted or are substituted by radicals selected from the group consisting of $C_1$–$C_9$-alkyl and hydroxyl, $C_1$–$C_4$-alkanes substituted by two or three phenol groups, di(hydroxphenyl) sulfones or mixtures of these phenols,
with
formaldehyde or formaldehyde-supplying compounds in a molar ratio of melamine, substituted melamine I and triazine II to formaldehyde within the range from 1:1.15 to 1:4.5.

2. The process of claim 1, wherein the substituted melamine I used is selected from the group consisting of 2-hydroxyethylamino-substituted melamine I, 2-hydroxyisopropylamino-substituted melamine I, 5-hydroxy-3-oxapentylamino-substituted melamine I and 6-aminohexylamino-substituted melamine I; wherein the condensation is carried out at a temperature of from 20 to 150° C. and at a pressure of from 100 to 500 kPa.

3. Condensation products as claimed in claims 1, wherein the phenol used is selected from the group consisting of phenol, 2,2-bis(4-hydroxyphenyl)propane and resorcinol.

4. A condensation product obtained by the process of claim 1.

5. A fiber produced from the condensation product defined in claim 4.

6. A foam produced from the condensation product defined in claim 4.

7. A molded article produced from the fiber defined in claim 5.

8. A molded article produced from the foam defined in claim 6.

* * * * *